(12) United States Patent
Heigl et al.

(10) Patent No.: US 7,780,351 B2
(45) Date of Patent: Aug. 24, 2010

(54) METHOD FOR DETERMINING GRAY-SCALE VALUES FOR VOLUME ELEMENTS OF BODIES TO BE MAPPED

(75) Inventors: Benno Heigl, Coburg (DE); Stefan Hoppe, Amberg (DE); Joachim Hornegger, Effeltrich (DE); Günter Lauritsch, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 253 days.

(21) Appl. No.: 12/008,943

(22) Filed: Jan. 15, 2008

(65) Prior Publication Data

US 2008/0181367 A1 Jul. 31, 2008

(30) Foreign Application Priority Data

Jan. 25, 2007 (DE) .................. 10 2007 003 877

(51) Int. Cl.
G01D 18/00 (2006.01)
(52) U.S. Cl. .......................................... 378/207; 378/4
(58) Field of Classification Search ................ 378/4, 378/207

See application file for complete search history.

(56) References Cited

U.S. PATENT DOCUMENTS

| | | | | |
|---|---|---|---|---|
| 5,319,693 | A | | 6/1994 | Eberhard et al. |
| 5,442,674 | A | * | 8/1995 | Picard et al. .................. 378/20 |
| 5,740,224 | A | * | 4/1998 | Muller et al. ................. 378/11 |
| 6,236,704 | B1 | * | 5/2001 | Navab et al. ................... 378/4 |
| 6,466,638 | B1 | * | 10/2002 | Silver et al. ..................... 378/4 |
| 2001/0031032 | A1 | * | 10/2001 | Proksa .......................... 378/15 |
| 2002/0075994 | A1 | * | 6/2002 | Shahidi et al. ................ 378/62 |
| 2003/0133533 | A1 | * | 7/2003 | Bruder et al. ................... 378/4 |
| 2003/0161433 | A1 | * | 8/2003 | Nishide et al. .................. 378/4 |
| 2003/0219093 | A1 | * | 11/2003 | Hagiwara ........................ 378/4 |
| 2004/0114707 | A1 | * | 6/2004 | Bruder et al. ................... 378/4 |
| 2005/0249327 | A1 | * | 11/2005 | Wink et al. ..................... 378/8 |
| 2005/0265523 | A1 | | 12/2005 | Strobel |
| 2006/0039537 | A1 | | 2/2006 | Strobel |
| 2007/0009078 | A1 | * | 1/2007 | Saito et al. ..................... 378/4 |

OTHER PUBLICATIONS

Hartley et al., "Multiple View Geometry in Computer Vision", Cambridge University Press, Jun. 2000, ISBN 0521623049.

Feldkamp et al., "Practical Cone-beam Algorithm", JOSA A1, 612 (1984), Journal of the Optical Society of America, Jun. 1984, pp. 612-619, vol. 1, No. 6.

(Continued)

*Primary Examiner*—Edward J Glick
*Assistant Examiner*—Alexander H Taningco

(57) ABSTRACT

The invention relates to a method for determining gray-scale values for volume elements of bodies to be mapped using an x-ray image recording system. When a body to be mapped is not mapped in full on a single projection image for a rotational position, a second projection image must be made and a virtual projection image derived from the two projection images, this being back-projected onto the volume elements. For calibration the present invention proposes making the same two projection images in each case at a calibration phantom and additionally a further projection image, corresponding to the position and orientation of the virtual projection image. As a result the mathematical relationships between the projection images and the virtual projection image and for the back-projection can be derived.

17 Claims, 3 Drawing Sheets

OTHER PUBLICATIONS

Norbert K. Strobel, Benno Heigl, Thomas M. Brunner, Oliver Schuetz, Matthias M. Mitschke, Karl Wiesent and Thomas Mertelmeier, "Improving 3D Image Quality of X-Ray C-Arm Imaging Systems by Using Properly Designed Pose Determination Systems for Calibrating the Projection Geometry", Medical Imaging 2003: Physics of Medical Imaging, Proceedings of SPIE, vol. 5030, pp. 943-954, Abstract.

Jens Wiegert et al., "3D ROI imaging for cone-beam computed tomography", International Congress Series 1268 (2004), pp. 7-12; Others.

* cited by examiner

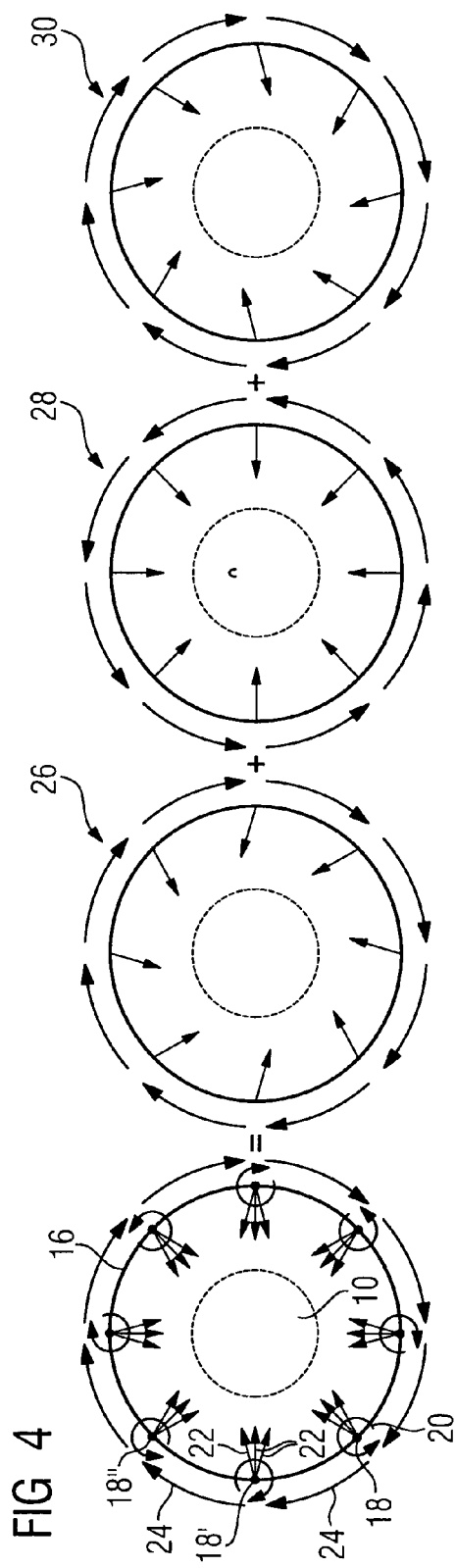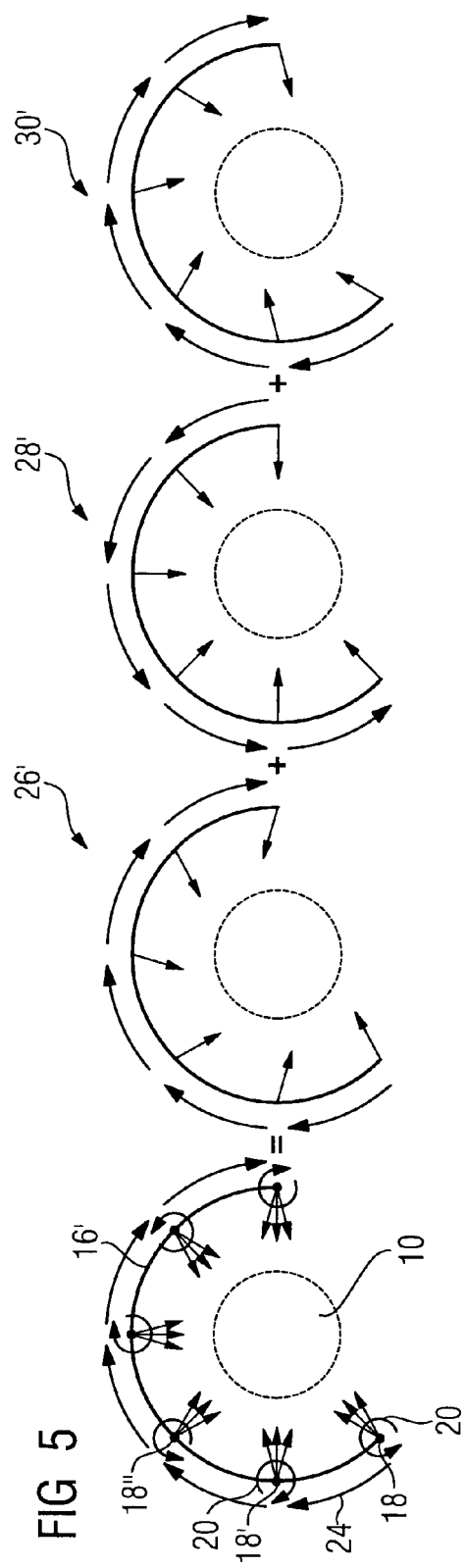

METHOD FOR DETERMINING GRAY-SCALE VALUES FOR VOLUME ELEMENTS OF BODIES TO BE MAPPED

CROSS REFERENCE TO RELATED APPLICATIONS

This application claims priority of German application No. 10 2007 003 877.3 filed Jan. 25, 2007, which is incorporated by reference herein in its entirety.

FIELD OF THE INVENTION

The invention relates to a method for determining gray-scale values for volume elements of bodies to be mapped using an x-ray image recording system having an x-ray source and x-ray detector.

BACKGROUND OF THE INVENTION

The method emerges directly from the method for reconstruction of a three-dimensional image volume described in DE 10 2006 041 033.5 published after the filing date of the present application. Whereas with conventional methods for determining gray-scale values for volume elements of bodies to be mapped at predetermined rotational positions of the x-ray image recording system a 2D x-ray image (projection image) is recorded in each case, DE 10 2006 041 033.5 deals with the problem that this projection image is not sufficient to fully map a body to be mapped. Instead, only parts of the body are mapped in a projection image. In DE 10 2006 041 033.5 the problem is solved in that at least two different projection images of such a body to be mapped are recorded in each case for the predetermined rotational positions of the x-ray image recording system. The projection images are not recorded randomly, but a constant relative position between the focal point of the x-ray source and the area of interest of the body to be mapped is common to the at least two different projection images, a triangle being formed for this purpose between the focal point and two points in the area of interest, said triangle being displaced by rotations about the focal point, in order to distinguish one of the different projection images from the other. The at least two different projection images are not directly back-projected in the method for reconstruction of a three-dimensional image volume. Instead, a virtual projection image is created, in which in contrast to the individual different real projection images the body to be mapped is actually displayed in full. To create the common virtual projection image, a predefined mapping rule is used. The virtual projection image is now used to calculate, using back projection onto the volume elements, contributions to the gray-scale values assigned to the rotational position, one contribution to each rotational position in each case. The contributions to all rotational positions are then summed to form the gray-scale values to be determined.

If as in this case back-projection is used, calibration is required. For example, when an x-ray C-arm is rotated, vibrations occur when the system is accelerated. The projection parameters for each recording position should now be determined under recording conditions during calibration. The projection parameters are normally summarized in a projection matrix. The projection parameters are used to described the projection geometry. For each point in the projection image it is determined which view ray determines the gray-scale value at this point, i.e. how the line appears from the focus of the x-ray source to the x-ray detector.

In connection with the method of filtered back-projection, the use of a "calibration phantom" is known, which is shown in FIG. 1 and designated there as a whole by 10. A calibration phantom is a body known by predetermined individual features. The mapping conditions, i.e. the projection parameters, are inferred from the mappings of the individual features. Details of the calibration phantom shown in FIG. 1 are described in the article by N. Strobel, B. Heigl, T. Brunner, O. Schütz, M. Mitschke, K. Wiesent, T. Mertelmeier: "Improving 3D Image Quality of X-Ray C-Arm Imaging Systems by Using Properly Designed Pose Determination Systems for Calibrating the Projection Geometry" from Medical Imaging 2003: Physics of Medical Imaging; edited by Yaffe, Martin J.; Antonuk, Larry E. in Proceedings of the SPIE, Vol. 5030, pp. 943-954, 2003.

The calibration phantom 10 consists of a plastic cylinder 12 transparent to x-rays, in which 108 balls 14 are embedded. The balls are made of non-corroding steel and thus act as markers in the x-ray images. The balls are arranged helically. The helical arrangement of the markers has the advantage that especially in the case of circular scanning tracks, as are normal with x-ray C-arms, sinusoidal curves can be identified in the projection images, i.e. as many markers as possible are optimally mapped simultaneously. The balls 14 of the calibration phantom can be of two different sizes: the small balls have a diameter of 1.6 mm, and the large balls a diameter of 3.2 mm. The choice of large and small balls for a particular location in the helix is effected by way of coding, producing binary coding thanks to the opportunity to provide two different sizes of ball. The coding is selected so that a partial sequence of eight balls is sufficient in the mapping if their different sizes can be identified in the projection image, to assign precisely which eight balls from the 108 balls have been mapped in the projection image. The calibration phantom 10 is used to determine the projection parameters for a (filtered) back-projection, the following steps being performed:

1.) Locating the 2D marker position in the projection image,

2.) Determining the sequence of the 2D marker position (along the helix), especially using a sinusoidal mapping of the helix, 3.) Assigning the 2D marker position to the 3D marker locations in the helix using the coding, 4.) Determining the projection matrix for each scanning point using the 2D-3D marker correspondences.

The problem of performing a calibration during the method for reconstruction of a three-dimensional image volume known from DE 10 2006 041 033.5 rests on the fact that although projection images are likewise recorded there, they are not themselves used for back-projection, but are initially mapped to a (common) virtual projection image, the virtual projection image only then being back-projected.

SUMMARY OF THE INVENTION

The object of the invention is to specify a detailed calibration rule for this method of determining gray-scale values for volume elements of bodies to be mapped (from DE 10 2006 041 033.5).

The object is achieved by a method having the features as claimed in the claims.

The inventive method is thus characterized in that prior to calibration for a body known by predetermined individual features (e.g. the calibration phantom 10 from FIG. 1) the predetermined rotational positions are run through and in each case the at least two different projection images and a further projection image of this body are recorded. In each case a mapping rule for the different projection images onto the further projection image is determined, and this mapping rule is used to calculate a virtual projection image. The virtual projection image is ideally merely an enlargement of the further projection image in size, so that the virtual projection image can later fulfill its task of showing the body to be mapped as fully as possible, which the individual projection images and thus the further projection image necessarily cannot do. The virtual projection image of the body whose predetermined individual features are known is now used, on the basis of the predetermined individual features mapped in the virtual projection image, to derive a mathematical rule (projection parameter, especially projection matrix) for the back-projection of the virtual projection image onto the volume elements. Calibration thus includes determining mapping rules for the different projection images onto the further projection image and a back-projection rule. These very rules are then used after calibration when determining the gray-scale values for volume elements of bodies to be mapped, namely the mapping rules are used to define the virtual projection image, and the mathematical rule is used for the back-projection of the virtual projection image.

The present invention emerges from the recognition that to determine the projection parameters it is not sufficient if the virtual projection image is defined by a mathematical rule from the outset. Instead, a real recorded projection image is required, e.g. a calibration phantom. The real recorded projection image is now selected so that its position and orientation can later define the virtual projection image. Of course it is conversely also possible to define the position and orientation of the virtual projection image first and then make recordings appropriate thereto. It should again be explicitly stated that the virtual projection image should be larger than the real projection images, so that bodies to be mapped can be mapped in full, since this is the purport of the method from DE 10 2006 041 033.5. However, the virtual projection image can easily be defined by linking other image sections, if the further real recorded projection image essentially defines the position and orientation.

In a first alternative of the invention the calibration phantom is selected in respect of the x-ray image recording system with a predetermined definition of the different projection images and of the further projection images such that during calibration at least the at least two different projection images only partially show the calibration phantom (the body known by predetermined individual features). Thus the subsequent situation is prepared during mapping of bodies which cannot be seen in full in the individual projection images. In this case the mapping rules must be successively tested. Those mapping rules are selected which minimize a clearance, e.g. which minimize the total using the squares of the difference of the gray-scale value in each case of a point in each case of one of the different projection images and of the gray-scale value of the determined point of the further projection image assigned to the one point in each case with the aid of the mapping.

If all projection images show the body known by individual features (the calibration phantom) in full during calibration, thus if either the calibration phantom is small enough or the two different projection images are suitably chosen, a mathematical rule for a back-projection onto the volume elements can be derived from each projection image, i.e. the at least two different projection images and the further projection image. It thus becomes possible to unambiguously assign points in the at least two different projection images to points on the further projection image in each case. If at least four pairs of such assigned points are determined, a precise calculation of the mapping rules for the different projection images onto the further projection image can be made on the basis of these pairs, e.g. a linear equation system which is easy to solve can be created using mathematical methods known per se.

BRIEF DESCRIPTION OF THE DRAWINGS

Preferred embodiments of the invention are described below with reference to the drawing, in which:

FIG. 4 illustrates how individual images are recorded when the x-ray image recording system is fully rotated to different rotational positions, FIG. 5 illustrates how individual images are recorded when the x-ray image recording system is not fully rotated to different rotational positions.

DETAILED DESCRIPTION OF THE INVENTION

Figure 1:
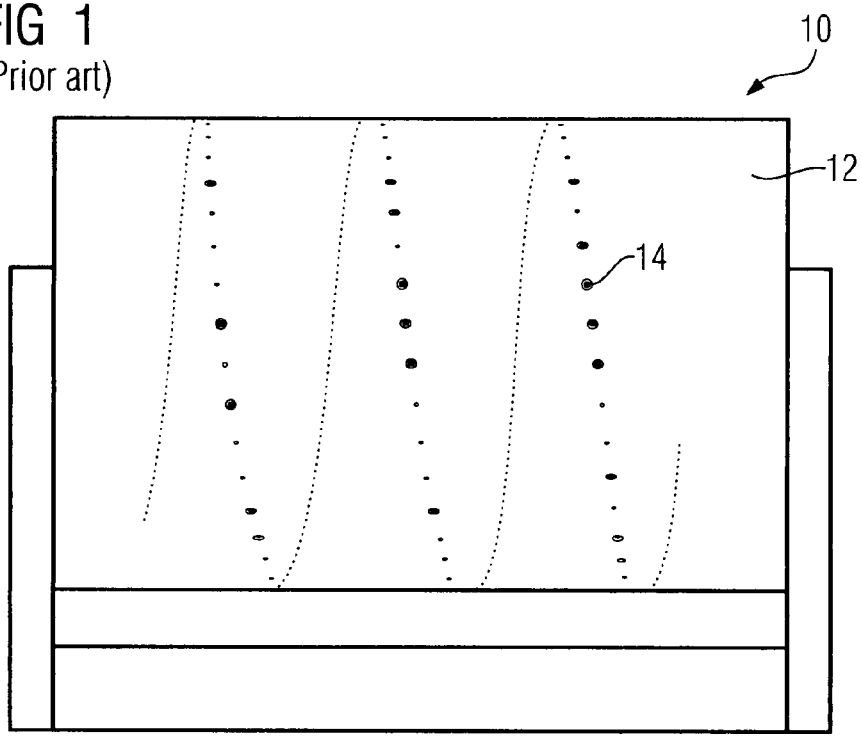
FIG. 1 shows a calibration phantom according to the prior art, which is used in the present invention.
Figure 2:
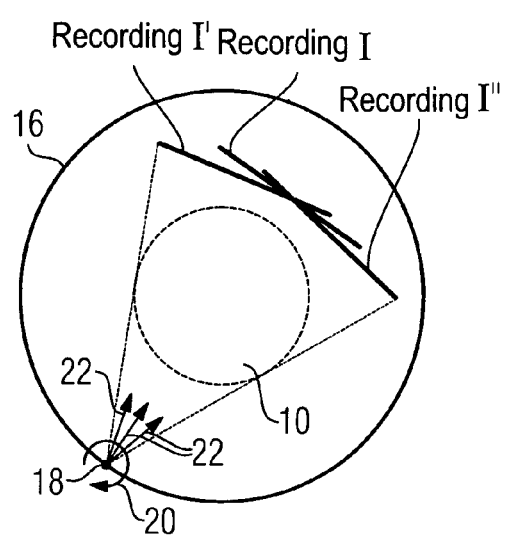
FIG. 2 illustrates how three overlapping projection images can be recorded.
Figure 3:
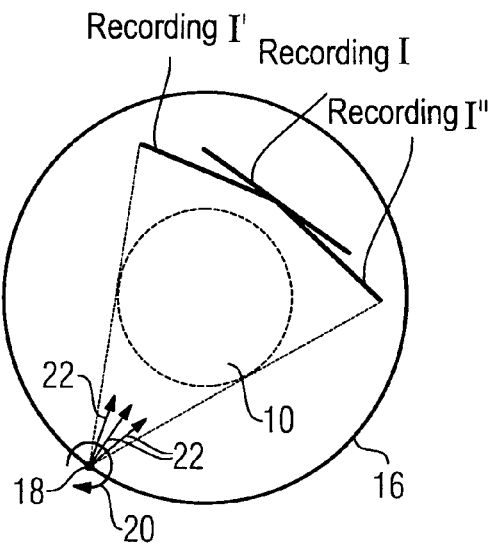
FIG. 3 illustrates how three projection images which overlap as little as possible can be recorded.

FIGS. 2 and 3 show a circular arc 16 defined by a fall rotation of an x-ray image recording system comprising x-ray source and x-ray detector, e.g. by a 360-degree rotation of an x-ray C-arm. A marked point 18 in each case indicates the origin of x-ray radiation, in other words the focus within an x-ray source. The point 18 is simultaneously a center of rotation for the x-ray source, the circular arrow 20 illustrating the rotation. The x-ray radiation is radiated in the direction of the arrows 22 in three different recordings I', I, I". The calibration phantom 10 from FIG. 1 is mapped if the maximum size for this is chosen. In this case the expansion of the x-ray radiation emitted by the x-ray source is not sufficiently large that all parts of the calibration phantom 10 are mapped on recording I', the first different projection image. Nor is the calibration phantom 10 fully visible on recording I", the second different projection image. It is now a matter of creating a virtual projection image from recordings I' and I" in the case of bodies subsequently to be mapped whose structure is of interest, from recordings I' and I". This virtual projection image should then show the body to be mapped in full. It is possible to arrange the virtual projection image so that it symbolizes a full recording in one direction, lying precisely between the direction in which the recording I' was made, and the direction in which recording I" was made. In other words the virtual projection image should correspond to a mean rotation in accordance with the arrow 20. To obtain information about the virtual projection image a recording is now actually made in the context of the calibration with the aid of the calibration phantom 10, the position and orientation of said recording corresponding precisely to the virtual projection image. This is recording I. In FIG. 2 recordings I' and I" overlap, but not in FIG. 3. Overlapping results in a redundancy when mapping particular structures. This is not absolutely necessary.

Whereas FIG. 2 and FIG. 3 illustrate the recording of projection images for just one rotational position of the x-ray image recording system, FIG. 4 and FIG. 5 show a plurality of such rotational positions. FIG. 4 illustrates that over the whole circumference of a circle 16 the x-ray radiation focus runs clockwise (arrow 24) through different points 18, 18' etc., three projection images being taken in each case, see arrows 22, corresponding to the recordings I', I and I" in FIG. 2 or 3. As can be seen in FIG. 4, the x-ray source can be rotated in accordance with the arrow 20 in each of the points 18, 18', 18". Instead of this, three individual passes with constant orientation of the x-ray source and of the x-ray detector are possible, which are characterized in FIG. 4 by 26, 28 and 30. The x-ray recording system with the x-ray source and the x-ray detector must be rotated once between passes 26 and 28 and once between passes 28 and 30.

FIG. 5 shows the case in which it is highly expedient for the inventive method if what takes place is not a rotation 16 of a complete circle corresponding to the arrows 24 in FIG. 4, but only a rotation of a partial circle 16' of e.g. 220 degrees corresponding to the arrows 24, it also being possible here for either a rotation about the points 18, 18', 18" etc. to take place, in each case corresponding to the arrow 20 or for the entire mapping to consist of three passes of the partial circle 16' corresponding to the designations 26', 28' and 30'.

The result is three recordings for each rotational position on the circle 16 (FIG. 4) or the partial circle 16' (FIG. 5), namely the two different projection recordings I' and I" plus a further projection image, the recording I. The recording I is used to derive a rule for mapping onto the other two recordings. Such a mapping is here called homography H' or H". A homography is a mapping rule, by which points of a 2D coordinates system are transferred to a different 2D coordinates system. Whenever two or more planes intersect a radiation beam, a homographic relationship exists between the corresponding intersection points of the different planes. If the points are expressed in homogeneous coordinates, this relationship can be formulated as linear mapping y=Hx, where x designates the original point, y the transformed point and the 3×3 matrix H the homographic transformation itself. Details of homographies can be taken from the book by R. Hartley and A. Zisserman: "Multiple View Geometry in Computer Vision", Cambridge University Press, Cambridge UK, Second Edition 2003.

Figure 6:
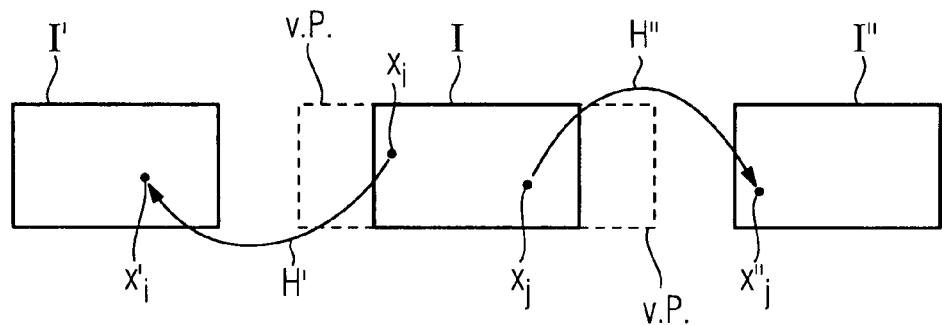
FIG. 6 illustrates the definition of the mapping rules of the further projection image onto the two different projection images.

The homographies H' and H", by which the recording I is mapped to the recording I' or I", are elucidated in FIG. 6. Because of the common position of the focus 18 the following relationship prevails in the three recordings:

$$x_i' = H' x_i \text{ and}$$

$$x_j'' = H'' x_j,$$

where $x_i$ and $x_j$ in FIG. 6 are pixel positions in recording I shown by way of example and $x_i'$ and $x_j''$ represent corresponding pixel positions in recording I' or I".

The homographies H' and H" must now be derived as a mapping rule in the context of the calibration.

Figure 7:
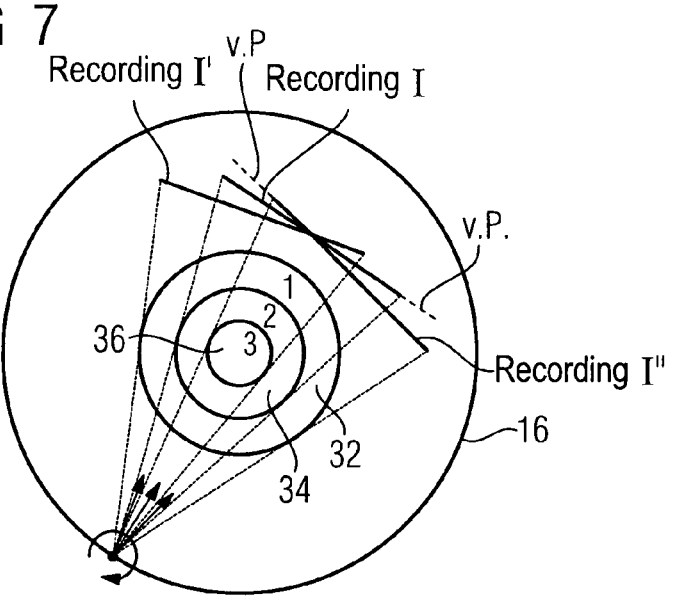
FIG. 7 illustrates different cases of how the calibration phantom from FIG. 1 is fully mapped in recordings according to FIG. 2.

The three situations illustrated in FIG. 7 can be distinguished:

FIG. 7 once again shows the circle 16 from FIG. 2 with three concentric circles as a mapping object. The outer circle 32 corresponds to the situation in FIG. 2, in which the calibration phantom 10 is so large that it is not mapped in full on any of the recordings I', I". The second circle 34 is so large that the calibration phantom, if it is this size, is mapped in full on recording I, but not on recordings I' and I". The inner circle 36 is so large that the calibration phantom, if it was exactly the same size, would be mapped in full on all three recordings I', I and I".

Generally the case of circle 32 prevails, or at most that of circle 34. The homographies H' and H" cannot then be mathematically derived exactly.

The homographies H' and H" are instead determined by minimization using the formula:

$$\operatorname*{argmin}_{H'}\left\{\sum_i (I'(H' x_i) - I(x_i))^2\right\}$$

and $$\operatorname*{argmin}_{H''}\left\{\sum_j (I''(H'' x_j) - I(x_j))^2\right\}.$$

Here $I(x_i)$ or $I(x_j)$ are the gray-scale values at the positions $x_i$ or $x_j$ of recording I. $I'(H' x_i)$ designates the gray-scale value at the position $x_i' = H' x_i$ of recording I', and $I''(H'' x_j)$ designates the gray-scale value at the position $x_j'' = H'' x_j$ of recording I". A prerequisite for this calculation is that the recordings I' and I on the one hand and I" and I on the other overlap to a sufficient extent and the pixel positions $x_i, x_j, x_i', x_j''$ always lie within this area of overlap. For minimization any known numeric method can be used, e.g. "steepest descent", in which the minimum is reached fastest in the direction of the steepest descent about a predetermined point. Other methods are described in the book by Hartley and Zisserman cited above.

While I is exactly the same size as I' and I", namely represents a real projection image, a virtual projection image v.P., represented in FIG. 6 by a dotted line as an enlargement of recording I, can be constructed using H' and H" on the basis of the whole recordings I' and I". The virtual projection image v.P. then generally maps in full the body to be mapped, and in particular in the case of the circle 32 from FIG. 7 the whole calibration phantom or the whole body to be mapped, even if recording I does not then do this alone.

Once the virtual projection image is determined, any calibration method can be used to determine the projection matrix, so that back-projection onto volume elements (voxels) is possible. When the calibration phantom 10 from FIG. 1 is used the above-mentioned four steps in the prior art can be used for the calibration, i.e. the calibration can be performed on the basis of the marker balls 14.

The minimization formulae mentioned for determining the homographies H' and H" apply if the calibration phantom is as large as the circles 32 and 34. If the calibration phantom is smaller, in other words is as big as the circle 36 and is thus mapped in all three recordings I', I and I", the homographies can be precisely mathematically determined. This is possible because each of the recordings I', I and I" allows a respective projection matrix P', P and P" to be derived, then one-to-one relationships between the mappings to be derived from the individual projection matrices, creating a basis for the solution in a linear equation system. This will not be dealt with further in detail here, but reference is made to the book by Hartley and Zisserman cited above.

The calibration is thus concluded by on the one hand the homographies H' and H" and on the other the projection matrix (e.g. called P), which applies for the virtual projection image, being determined. Using these three mathematical rules it is then possible to perform the method as claimed in DE 10 2006 041 033.5. To use the terms from the present application: Then only the recordings I' and I" are made at any body to be mapped, this body to be mapped then replacing the calibration phantom 10 in FIG. 4 or 5 and the mean recording per rotation position in each case, i.e. the recording I, in particular not having to be made. Instead, by using the homographies H' and H" the virtual projection image is derived. This is then used in turn, utilizing the projection matrix (P) for back-projection onto the volume elements.

The invention claimed is:

1. A method for acquiring and applying a calibration with a calibration body to determine gray-scale values for volume elements of a second body to be mapped using an x-ray image recording system, comprising:
providing an x-ray image recording system comprising a C-arm including an x-ray source and an x-ray detector positionable about an arc so that the source can be sequentially positioned in multiple focal positions along the arc wherein each focal position corresponds to an origin of x-ray radiation;
with a first focal position as a center of rotation for the source, positioning the source at multiple rotational positions to generate radiation along different paths to create a first series of different projection images, with each projection image in the first series based on generation of radiation from the same origin;
with the source in the first focal position, recording in the first series of projection images at least two different projection images of the calibration body and a further projection image of the calibration body, each projection image corresponding to a different rotational orientation about the first position, wherein individual features of the calibration body are predetermined and known;
determining a mapping rule for mapping the at least two different projection images onto the further projection image;
applying the mapping rule to calculate a virtual projection image, portions of which cannot be shown by individual recordings in the first series; and
applying the virtual projection image, on the basis of the mapping rule, to derive a mathematical rule for the back projection of the virtual projection image onto the volume elements of the calibration body based on the individual features mapped between the two different projection images and the further projection image to generate the virtual projection image; and
applying the mapping rule and the mathematical rule to determine gray scale values for the volume elements of the second body in a back projection of a virtual image of the second body.

2. The method as claimed in claim 1, wherein a plurality of contributions to the gray-scale values are calculated at a plurality of focal positions about the arc of the x-ray image recording system.

3. The method as claimed in claim 2, wherein the gray-scale values are determined by adding the contributions.

4. The method as claimed in claim 1, wherein a calibration is acquired at additional ones of the focal positions of the x-ray image recording system wherein, with each additional focal position as a center of rotation for the source, by:
positioning the source at multiple rotational positions to generate radiation along different paths to create an additional series of different projection images, with each projection image in the additional series based on generation of radiation from the same origin.

5. The method as claimed in claim 1, wherein the second body is partially shown in the at least two different projection images.

6. The method as claimed in claim 5, wherein the mapping rule minimizes a clearance regarding the gray-scale values of one of the at least two different projection images and the gray-scale values of the further projection image determined by mapping.

7. The method as claimed in claim 1, wherein the further body is fully shown in the at least two different projection images.

8. The method as claimed in claim 7, wherein the mathematical rule is derived from the at least two different projection images and the further projection image.

9. The method as claimed in claim 8, wherein at least four pairs of points of one of the at least two different projection images are assigned to the further projection image.

10. The method as claimed in claim 9, wherein the mapping rule is calculated based on the pairs of the assigned points.

11. A method for determining gray-scale values for volume elements of a first body to be mapped using an x-ray image recording system, comprising:
providing an x-ray image recording system comprising a C-arm including an x-ray source and an x-ray detector positionable about an arc so that the source can be sequentially positioned in multiple focal positions along the arc wherein each focal position corresponds to an origin of x-ray radiation;
recording at least a pair of different projection images of a calibration body and a further projection image of the calibration body at each of the focal positions of the x-ray image recording system, individual features of the calibration body being predetermined and known;
for each of the focal positions, mapping at least the pair of different projection images onto the further projection image;
determining one or more mapping rules for mapping each pair of projection images on to the further projection image acquired from the same focal position as the pair and calculating therewith a plurality of virtual projection images of the calibration body, wherein a portion of each virtual projection image cannot be shown by an individual one in the pair of projection images used to form the virtual projection image;
applying multiple ones of the virtual projection images to derive one or more mathematical rules for back-projection of the virtual projection images onto the volume elements of the calibration body based on individual features mapped in the virtual projection images; and
applying the mapping rule and the mathematical rule to determine gray scale values for the volume elements of the first body in a back projection of a virtual image of the first body.

12. The method as claimed in claim 11, wherein the calibration body is only partially shown in each of the at least two different projection images.

13. The method as claimed in claim 12, wherein the mapping rules minimize a clearance regarding the gray-scale values of one of the at least two different projection images and the gray-scale values of the further projection image determined by mapping.

14. The method as claimed in claim 11, wherein the calibration body is fully showed shown in the at least two different projection images.

15. The method as claimed in claim 14, wherein the mathematical rule is derived from the at least two different projection images and the further projection image.

16. The method as claimed in claim 15, wherein at least four pairs of points of one of the at least two different projection images are assigned to the further projection image.

17. The method as claimed in claim 16, wherein the mapping rules are calculated based on the pairs of the assigned points.

* * * * *